United States Patent
Lange

(10) Patent No.: US 7,171,680 B2
(45) Date of Patent: Jan. 30, 2007

(54) METHOD AND APPARATUS FOR ELECTRO-BIOMETRIC IDENTITY RECOGNITION

(75) Inventor: Daniel H. Lange, Caesarea (IL)

(73) Assignee: IDesia Ltd., Caesarea (IL)

( * ) Notice: Subject to any disclaimer, the term of this patent is extended or adjusted under 35 U.S.C. 154(b) by 0 days.

(21) Appl. No.: 10/522,851

(22) PCT Filed: Jul. 24, 2003

(86) PCT No.: PCT/US03/23016

§ 371 (c)(1), (2), (4) Date: Jul. 29, 2005

(87) PCT Pub. No.: WO2004/012388

PCT Pub. Date: Feb. 5, 2004

(65) Prior Publication Data

US 2006/0013445 A1 Jan. 19, 2006

Related U.S. Application Data

(60) Provisional application No. 60/398,832, filed on Jul. 29, 2002.

(51) Int. Cl.
*G06F 7/04* (2006.01)
*H04K 1/00* (2006.01)
*G06K 9/00* (2006.01)

(52) U.S. Cl. .............................. 726/5; 713/186; 382/115
(58) Field of Classification Search ................. 726/5
See application file for complete search history.

(56) References Cited

U.S. PATENT DOCUMENTS 4,239,048 A * 12/1980 Steuer ........................ 600/479

(Continued)

FOREIGN PATENT DOCUMENTS

EP 1 081 662 A2 3/2001

(Continued)

OTHER PUBLICATIONS

Bao et al, Physiological Signal Based Entity Authentication for Body Area Sensor Networks and Mobile Healthcare Systems, 2005, IEEE, pp. 2455-2458.*

(Continued)

*Primary Examiner*—Christopher Revak
*Assistant Examiner*—Aravind K Moorthy
(74) *Attorney, Agent, or Firm*—Jones Day

(57) ABSTRACT

A method and apparatus for electro-biometric identity recognition or verification, producing and storing a first biometric signature that identifies a specific individual by forming the difference between a representation of the heartbeat pattern of the specific individual and a stored representation of common features of the heartbeat patterns of a plurality of individuals; after the producing step, obtaining a representation of the heartbeat pattern of a selected individual and producing a second biometric signature by forming the difference between the heartbeat pattern of the selected individual and the stored representation of common features of the heartbeat patterns of the plurality of individuals; and comparing the second biometric signature with the first biometric signature to determine whether the selected individual is the specific individual.

27 Claims, 5 Drawing Sheets

U.S. PATENT DOCUMENTS

| | | | |
|---|---|---|---|
| 4,685,465 A | 8/1987 | Klitgaard et al. | |
| 5,534,855 A | 7/1996 | Shockley et al. | |
| 5,892,824 A | 4/1999 | Beatson et al. | |
| 6,070,141 A | 5/2000 | Houvener et al. | |
| 6,231,346 B1 | 5/2001 | Sagi-Dolev | |
| 6,246,769 B1 * | 6/2001 | Kohut | 380/45 |
| 6,260,300 B1 | 7/2001 | Klebes et al. | |
| 6,293,904 B1 | 9/2001 | Blazey et al. | |
| 6,310,966 B1 | 10/2001 | Dulude et al. | |
| 6,335,688 B1 | 1/2002 | Sweatte | |
| 6,367,016 B1 | 4/2002 | Lambert et al. | |
| 6,483,929 B1 | 11/2002 | Murakami et al. | |
| 6,487,662 B1 | 11/2002 | Kharon et al. | |
| 6,490,680 B1 | 12/2002 | Scheidt et al. | |
| 6,633,090 B2 | 10/2003 | Harter et al. | |
| 6,961,448 B2 * | 11/2005 | Nichols et al. | 382/115 |
| 2001/0016311 A1 | 8/2001 | Sagi-Dolev | |
| 2001/0031071 A1 | 10/2001 | Nichols et al. | |
| 2001/0031602 A1 | 10/2001 | Sagi-Dolev | |
| 2001/0035814 A1 | 11/2001 | Uchida | |
| 2002/0021601 A1 | 2/2002 | Chomenky | |
| 2002/0073306 A1 | 6/2002 | Aluzzo et al. | |
| 2002/0094111 A1 | 7/2002 | Puchek et al. | |
| 2002/0138768 A1 | 9/2002 | Murakami et al. | |
| 2002/0154036 A1 | 10/2002 | Flick | |
| 2002/0184500 A1 | 12/2002 | Maritzen et al. | |
| 2002/0193142 A1 | 12/2002 | Stavenow et al. | |
| 2003/0023855 A1 | 1/2003 | Keogh et al. | |
| 2003/0048000 A1 | 3/2003 | Harter et al. | |
| 2003/0098774 A1 | 5/2003 | Chornenky | |
| 2003/0098776 A1 | 5/2003 | Friedli | |
| 2003/0113001 A1 | 6/2003 | Kato et al. | |
| 2003/0115165 A1 | 6/2003 | Hoya | |
| 2003/0128867 A1 * | 7/2003 | Bennett | 382/115 |
| 2003/0135097 A1 | 7/2003 | Wiederhold et al. | |
| 2004/0010724 A1 | 1/2004 | Brown et al. | |
| 2004/0036574 A1 | 2/2004 | Bostrum | |
| 2004/0091138 A1 | 5/2004 | Lee | |
| 2004/0108377 A1 | 6/2004 | Rietveld | |
| 2004/0193068 A1 | 9/2004 | Burton et al. | |
| 2005/0281439 A1 * | 12/2005 | Lange | 382/115 |
| 2006/0008128 A1 * | 1/2006 | Setlak et al. | 382/124 |
| 2006/0075257 A1 * | 4/2006 | Martis et al. | 713/186 |
| 2006/0136744 A1 * | 6/2006 | Lange | 713/186 |
| 2006/0204048 A1 * | 9/2006 | Morrison et al. | 382/115 |
| 2006/0241975 A1 * | 10/2006 | Brown | 702/2 |

FOREIGN PATENT DOCUMENTS

| | | |
|---|---|---|
| EP | 1 120 757 A2 | 8/2001 |
| EP | 1 318 481 A1 | 6/2003 |
| EP | 1353292 A1 * | 10/2003 |
| EP | 1 415 683 A1 | 5/2004 |
| EP | 1 418 486 A2 | 5/2004 |
| WO | WO 84/04815 | 12/1984 |
| WO | WO 07/15032 | 4/1997 |
| WO | WO 98/13791 | 4/1998 |
| WO | WO 99/23614 | 5/1999 |
| WO | WO 00/46756 | 8/2000 |
| WO | WO 00/65292 | 11/2000 |
| WO | WO 00/70545 | 11/2000 |
| WO | WO0143338 A1 * | 6/2001 |
| WO | WO 01/49369 A1 | 7/2001 |
| WO | WO 01/71642 A2 | 9/2001 |
| WO | WO 02/21763 A1 | 3/2002 |
| WO | WO 02/27686 A1 | 4/2002 |
| WO | WO 02/057998 A1 | 7/2002 |
| WO | WO 02/084602 A1 | 10/2002 |
| WO | WO 02/093330 A2 | 11/2002 |
| WO | WO 02/098054 A1 | 12/2002 |
| WO | WO 03/000015 A2 | 1/2003 |
| WO | WO 03/000015 A3 | 1/2003 |
| WO | WO 03/009113 A1 | 1/2003 |
| WO | WO 03/029048 A2 | 4/2003 |
| WO | WO 03/045740 A2 | 6/2003 |
| WO | WO 2004/010372 A1 | 1/2004 |
| WO | WO 2004/012388 A1 | 2/2004 |
| WO | WO 2004/048947 A1 | 6/2004 |
| WO | WO 2004/057546 A2 | 7/2004 |

OTHER PUBLICATIONS

Bao et al, Physiological Signal Based Entity Authentication for Body Area Sensor Networks and Mobile Healthcare Systems, 2005, IEEE, pp. 2455-2458.*

Biel, L., et al., 2001, "ECG Analysis: A New Approach in Human Identification," IEEE Transactions on Instrumentation and Measurement, vol. 50, No. 3, pp. 808-812.

Bolle, R.M., et al., "Guide to Biometrics," Springer-Verlag, 2003 (ISBN: 0-387-40089-3), pp. 8-10.

Mangona, A., et al., 2003, "Impact of age on QT interval and QT dispersion in healthy subjects: a regression analysis," Age and Ageing, vol. 32, pp. 326-331.

Tompkinss, W.J., et al., "A Portable Microcomputer-Based System for Biomedical Applications," Biomedical Sciences Intrumentation, Apr. 17-18, 1978, pp. 61-66, vol. 14, RMBS-ISA, USA.

Chien, I.C., et al., "Computer Methods for Analysing the High-Frequency Electrocardiogram," Medical & Biological Engineering & Computing, May 1980, pp. 303-312, vol. 18, No. 3, International Federation for Medical & Biological Engineering, England.

Kim, Y., et al., "Forward and Inverse High-Frequency Electrocardiography," Medical & Biological Engineering & Computing, Jan. 1981, pp. 11-22, vol. 19, No. 1, International Federation for Medical & Biological Engineering, England.

Abenstein, J.P., et al., "A New Data-Reduction Algorithm for Real-Time ECG Analysis," IEEE Transactions on Biomedical Engineering, Jan. 1982, pp. 43-48, vol. BME-29, No. 1, IEEE Engineering in Medicine and Biology Society, University of Wisconsin, Madison, WI, USA.

Thakor, N.V., et al., "A Battery-Powered Digital Modem for Telephone Transmission of ECG Data," IEEE Transactions on Biomedical Engineering, May 1982, pp. 355-359, vol. BME-29, No. 5, IEEE Engineering in Medicine and Biology Society, University of Wisconsin, Madison, WI, USA.

Tompkins, W.J., "Trends in Ambulatory Electrocardiography," IEEE Transactions on Biomedical Engineering, Aug. 1982, p. 600, vol. BME-29, No. 8, IEEE Engineering in Medicine and Biology Society, University of Wisconsin, Madison, WI, USA.

Weisner, S.J., et al., "A Compact, Microprocessor-Based ECG ST-Segment Analyzer for the Operating Room," IEEE Transactions on Biomedical Engineering, Sep. 1982, pp. 642-649, vol. BME-29, No. 9, IEEE Engineering in Medicine and Biology Society, University of Wisconsin, Madison, WI, USA.

Sahakian, A.V., et al., "A Microprocessor-Based Arrhythmia Monitor/Recorder for the Operating and Recovery Rooms," Medical Instrumentation, Mar.-Apr. 1983, pp. 131-134, vol. 17, No. 2, University of Wisconsin, Madison, WI, USA.

Furno, G.S., et al., "A Learning Filter for Removing Noise Interference," IEEE Transactions on Biomedical Engineering, Apr. 1983, pp. 31-34, vol. BME-30, No. 4, IEEE Engineering in Medicine and Biology Society, University of Wisconsin, Madison, WI, USA.

GE, J., et al., "High-Frequency ECG Feature Recognition Using a High Level Language," Biomedical Sciences Instrumentation, Apr. 18-19, pp. 31-34, vol. 19, RMBS-ISA, USA.

Thakor, N.V., et al., "Optimal QRS Detector," Medical & Biological Engineering & Computing, May 1983, pp. 343-350, vol. 21, No. 3, Int'l Federation for Medical & Biological Engineering, England.

Ahlstrom, M.L., et al., "Automated High-Speed Analysis of Holter Tapes with Microcomputers," IEEE Transactions on Biomedical Engineering, Oct. 1983, pp. 651-657, vol. BME-30, No. 10, IEEE Engineering in Medicine and Biology Society, University of Wisconsin, Madison, WI, USA.

Thakor, N.V., et al., "Design, Implementation and Evaluation of a Microcomputer-Based Portable Arrhythmia Monitor," Medical &

Biological Engineering & Computing, Mar. 1984, pp. 151-159, vol. 22, No. 2, Int'l Federation for Medical & Biological Engineering, England.

Thakor, N.V., et al., "Estimation of QRS Complex Power Spectra for Design of a QRS Filter," IEEE Transactions on Biomedical Engineering, Nov. 1984, pp. 702-706, vol. BME-31, No. 11, IEEE Engineering in Medicine and Biology Society, University of Wisconsin, Madison, WI, USA.

Pan, J., et al., "A Real-Time QRS Detection Algorithm," IEEE Transactions on Biomedical Engineering, Mar. 1985, pp. 230-236, vol. BME-32, No. 3, IEEE Engineering in Medicine and Biology Society, University of Wisconsin, Madison, WI, USA.

Ahlstrom, M.L., et al., "Digital Filters for Real-Time ECG Signal Processing Using Microprocessors," IEEE Transactions on Biomedical Engineering, Sep. 1985, pp. 708-713, vol. BME-32, No. 9, IEEE Engineering in Medicine and Biology Society, University of Wisconsin, Madison, WI, USA.

GE, J.G., et al., "High-Frequency Electrocardiogram Analyzer," IEEE Transactions on Biomedical Engineering, Dec. 1986, pp. 1137-1140, vol. BME-33, No. 12, IEEE Engineering in Medicine and Biology Society, University of Wisconsin, Madison, WI, USA.

Hamilton, P.S., et al., "Quantitative Investigation of QRS Detection Rules Using the MIT/BIH Arrhythmia Database," IEEE Transactions on Biomedical Engineering, Dec. 1986, pp. 1157-1165, vol. BME-33, No. 12, IEEE Engineering in Medicine and Biology Society, University of Wisconsin, Madison, WI, USA.

Hamilton, P.S., et al., "Compression of the Ambulatory ECG by Average Beat Subtraction and Residual Differencing," IEEE Transactions on Biomedical Engineering, Mar. 1991, pp. 253-259, vol. 38, No. 3, Dept. of Electrical and Computer Engineering, University of Wisconsin, Madison, WI, USA.

Hamilton, P.S., et al., "Theoretical and Experimental Rate Distortion Performance in Compression of Ambulatory ECG's," IEEE Transactions on Biomedical Engineering, Mar. 1991, pp. 260-266, vol. 38, No. 3, Dept. of Electrical and Computer Engineering, University of Wisconsin, Madison, WI, USA.

Xue, Q., et al., "Neural-Network-Based Adaptive Matched Filtering for QRS Detection," IEEE Transactions on Biomedical Engineering, Apr. 1992, pp. 317-329, vol. 39, No. 4, Dept. of Electrical and Computer Engineering, University of Wisconsin, Madison, WI, USA.

Hu, Y.H., et al., "Applications of Artificial Neural Networks for ECG Signal Detection and Classification," Journal of Electrocardiology, 1993, pp. 66-73, vol. 26 Supplement, Churchill Livingstone, Madison, WI, USA.

Luo, S., et al., "Parameter Evaluation of the Inverse Power-Law Spectrum of Heart Rate. A Quantitative Approach for ECG Arrhythmia Analysis," Journal of Electrocardiology, 1994, pp. 46-52, vol. 27 Supplement, Churchill Livingstone, Madison, WI, USA.

Panescu, D., et al., "A Database of Cardiac Arrhythmias," Academic Emergency Medicine, Jan. 1995, pp. 46-49, vol. 2, No. 1, University of Wisconsin, Madison, WI, USA.

Afonso, V.X., et al., "Detecting Ventricular Fibrillation: Selecting the Appropriate Time-Frequency Analysis Tool for the Application," IEEE Engineering in Medicine & Biology, Mar./Apr. 1995, pp. 152-159, vol. 14, No. 2, USA.

Afonso, V.X., et al., "Comparing Stress ECG Enhancement Algorithms: With an Introduction to a Filter Bank Based Approach," IEEE Engineering in Medicine & Biology, May/Jun. 1996, pp. 37-44, vol. 15, No. 3, USA.

Hu, Y.H., et al., "A Patient-Adaptable ECG Beat Classifier Using a Mixture of Experts Approach," IEEE Transactions on Biomedical Engineering, Sep. 1997, pp. 891-900, vol. 44, No. 9, Dept. of Electrical and Computer Engineering, University of Wisconsin, Madison, WI, USA.

Afonso, V., et al., "Use of Filter Banks in ECG Processing," Biomedical Engineering—Applications, Basis & Communications, Oct. 25, 1997, pp. 297-302, vol. 9, No. 5, Dept. of Electrical & Computer Engineering, University of Wisconsin, Madison, WI, USA.

Afonso, Valtino X., et al., "ECG Beat Detection Using Filter Banks," IEEE Transactions on Biomedical Engineering, Feb. 1999, pp. 192-202, vol. 46, No. 2, Endocardial Solutions, Inc., Saint Paul, MN, USA.

Wieben, O., et al., "Classification of Premature Ventricular Complexes Using Filter Bank Features, Induction of Decision Trees and a Fuzzy Rule-Based System," Medical & Biological Engineering & Computing, Sep. 1999, pp. 560-565, vol. 37, No. 5, Dept. of Electrical & Computer Engineering, University of Wisconsin, Madison, WI, USA.

Kyoso, Masaki, et al., "Development of an ECG Identification System," Papers from 23rd Annual Int'l Conference of the IEEE Engineering in Medicine and Biology Society, Oct. 25-28, 2001, Dept. of Information and Computer Sciences, Kanagawa Inst. of Technology, Istanbul, Turkey.

Harland, C.J., et al., "Electric potential probes—new directions in the remote sensing of the human body," Meas. Sci. Technol. (2002) 163-169, vol. 13, IOP Publishing Ltd., UK.

* cited by examiner

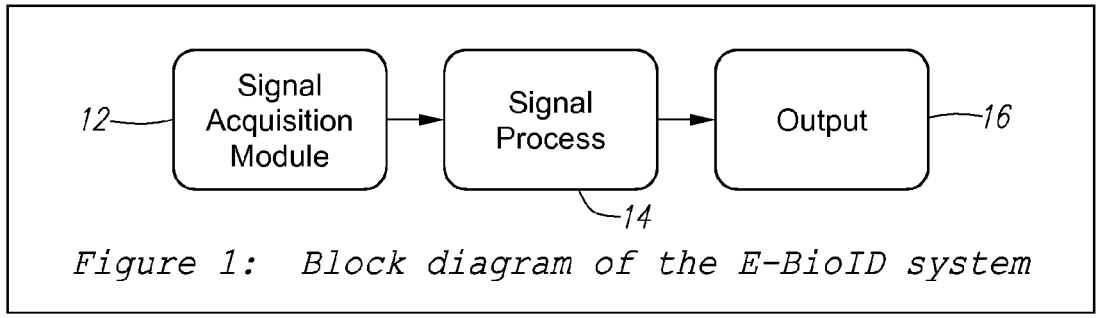
Figure 1: Block diagram of the E-BioID system
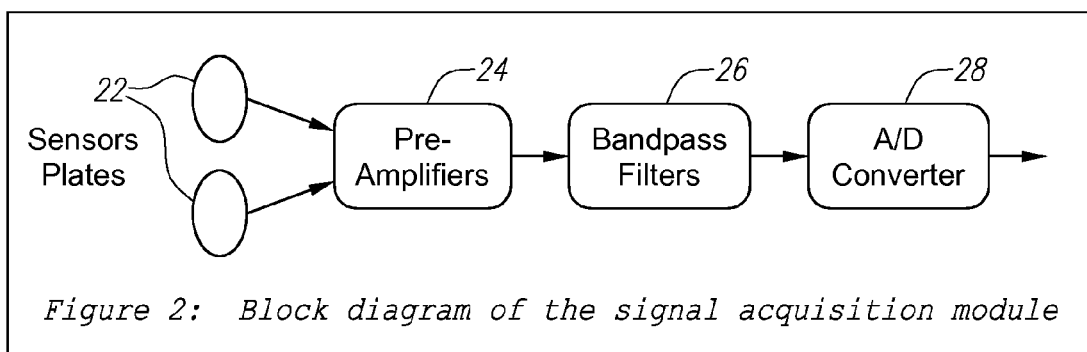
Figure 2: Block diagram of the signal acquisition module
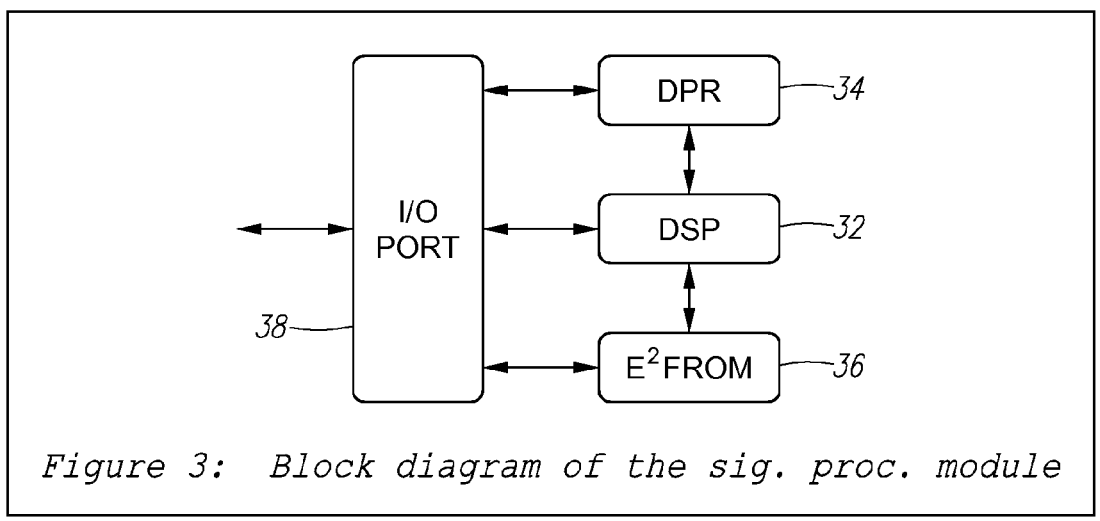
Figure 3: Block diagram of the sig. proc. module

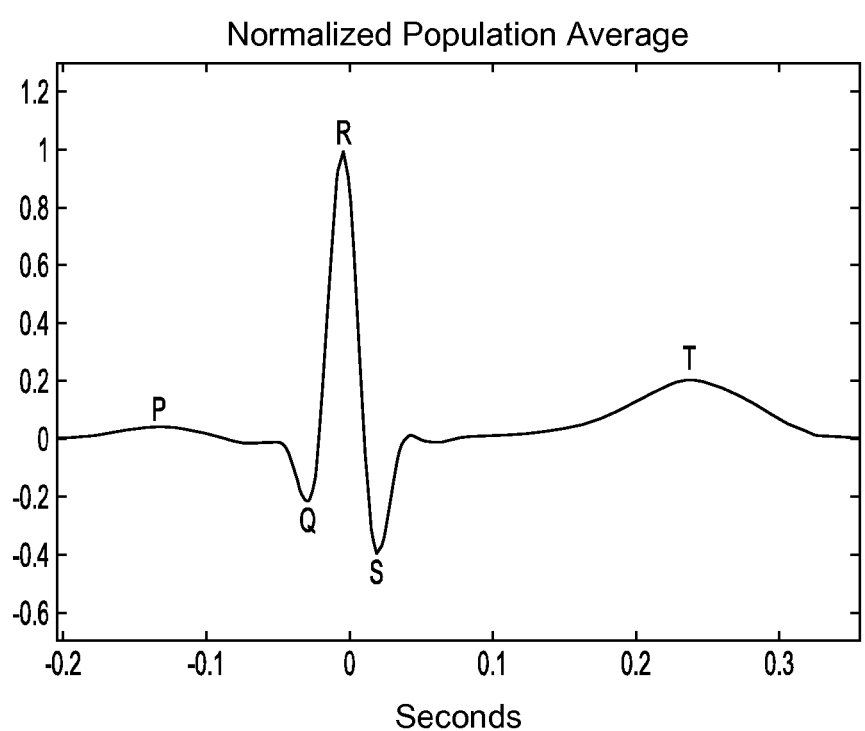
Figure 4: Normalized grand-average

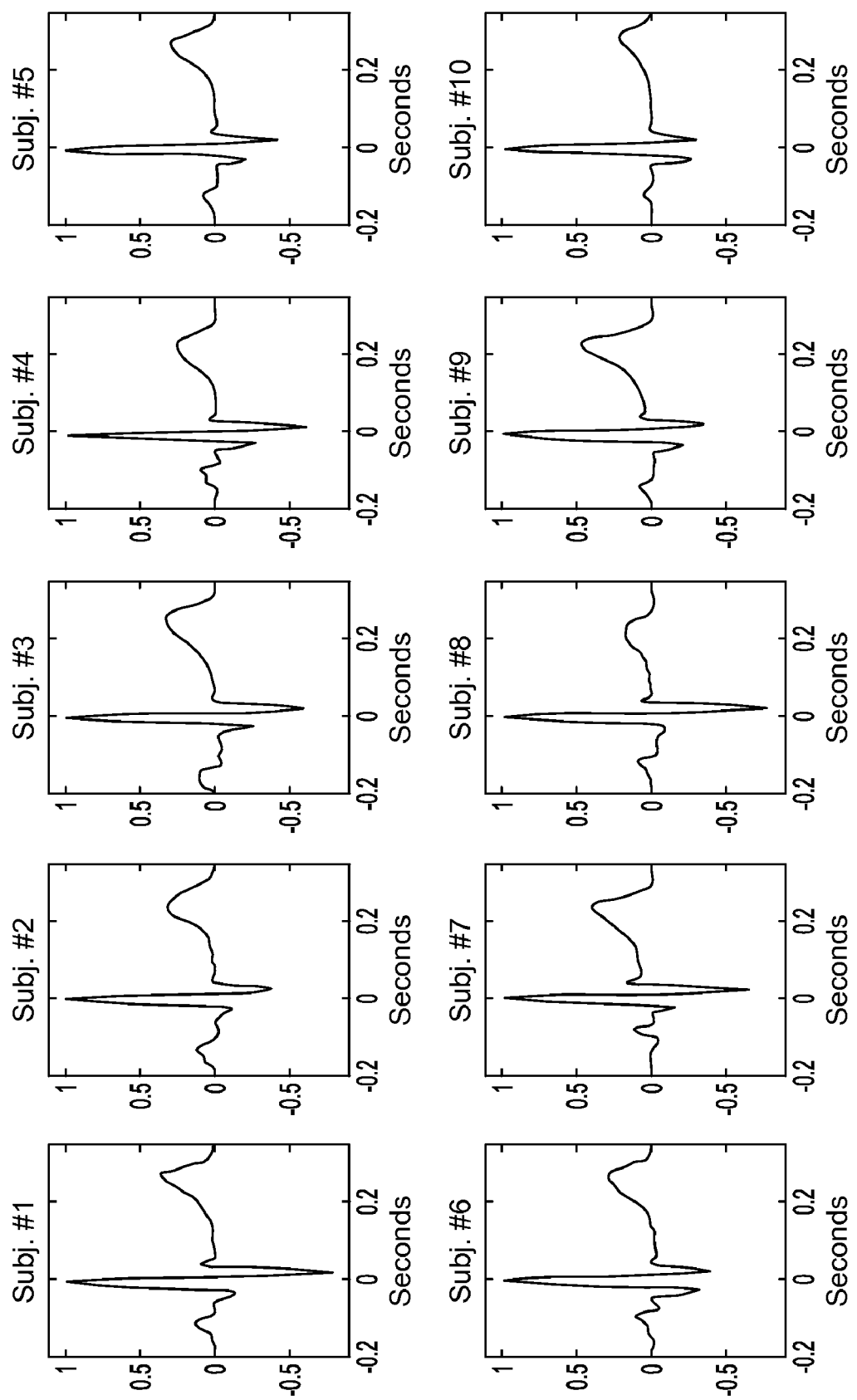
Figure 5: Electro-cardiologic signals of ten subjects

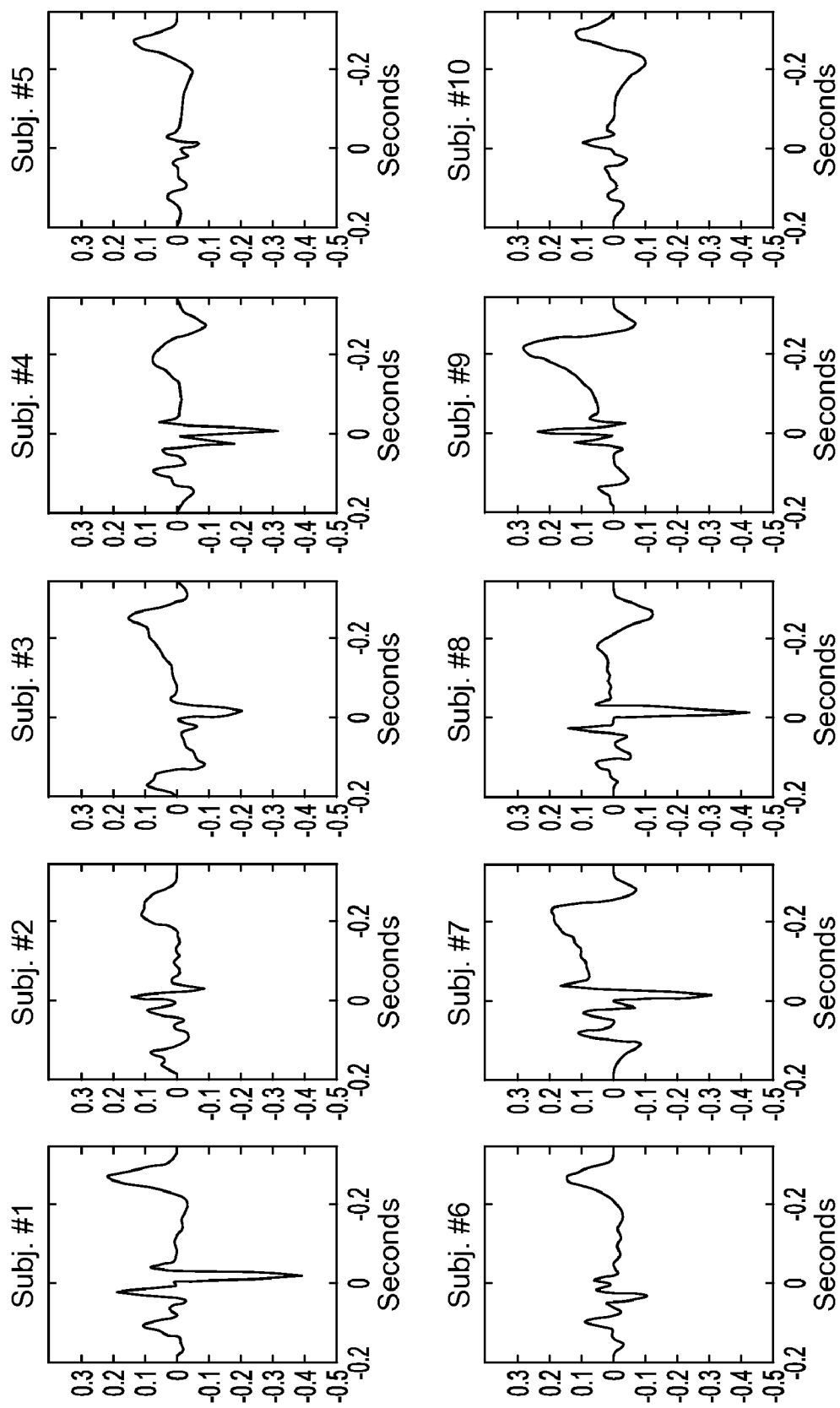
Figure 6: Signature templates of the above ten subjects

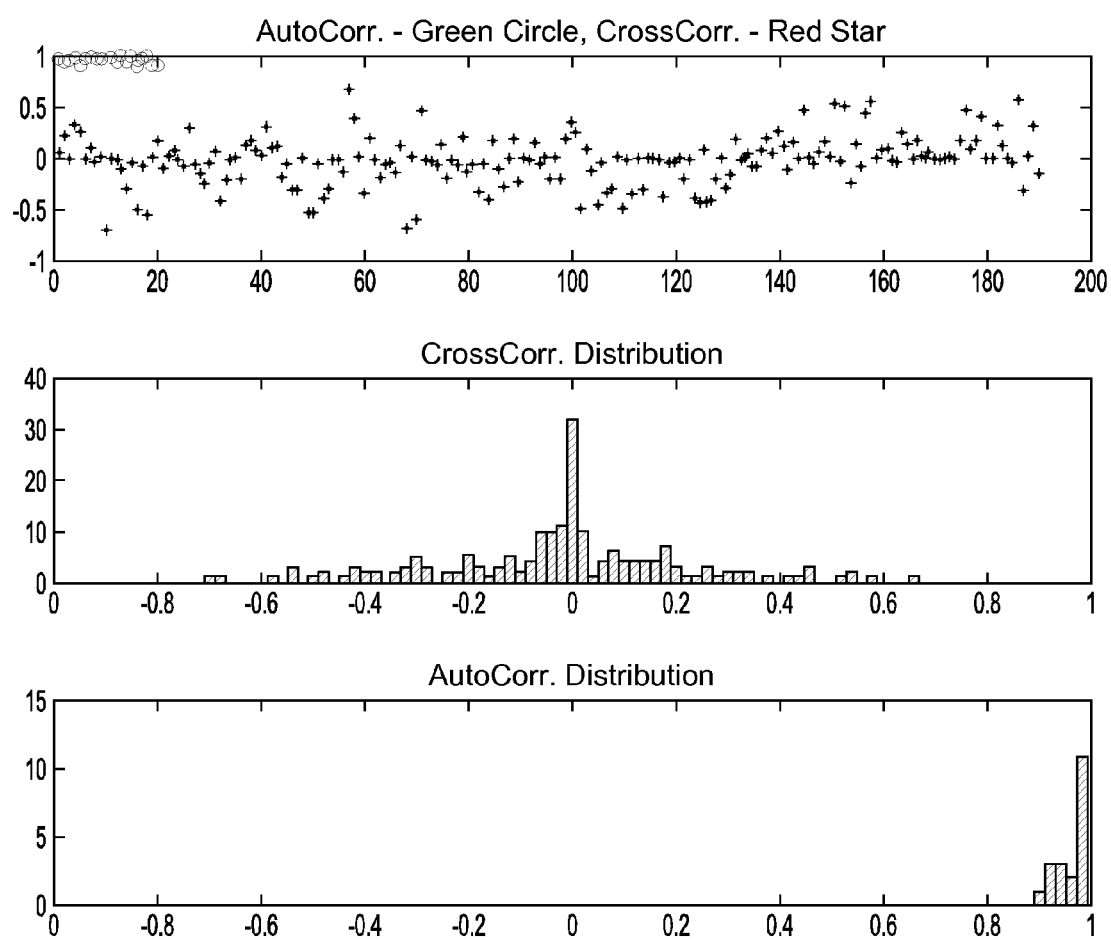
Figure 7: Distributions of correlation data

METHOD AND APPARATUS FOR ELECTRO-BIOMETRIC IDENTITY RECOGNITION

CROSS-REFERENCE TO RELATED APPLICATION

This application claims the benefit of U.S. Provisional application 60/398,832, filed on Jul. 29, 2002, and the entire disclosure of which is incorporated herein by reference.

BACKGROUND OF THE INVENTION

The present invention relates to acquisition, processing, and analysis of electro-biometric signals. More particularly, the present invention relates to systems and methods for electro-biometric identification and verification of a person's identity.

The present invention provides a system and method for electro-biometric identification and verification of a person's identity by bioelectric signal acquisition, processing, and analysis.

Identity recognition plays an important role in numerous facets of life, including automatic banking services, e-commerce, e-banking, e-investing, e-data protection, remote access to resources, e-transactions, work security, anti-theft devices, criminologic identification, secure entry, and entry registration in the workplace.

Utilized alone or integrated with other technologies such as smart cards, encryption keys, and digital signatures, biometrics are expected to pervade nearly all aspects of the economy and our daily lives.

Computerized systems use passwords and personal identification numbers (PIN) for user recognition. To maintain security, passwords have to be changed on a regular basis, imposing a substantial burden on the users.

Several advanced technologies have been developed for biometric identification and verification of a person's identity, the leading of which are fingerprint recognition, retina and iris recognition, face recognition, and voice recognition. However, these technologies have penetrated only limited markets due to complicated and unfriendly acquisition modalities, sensitivity to environmental parameters such as lighting conditions and background noise, and high cost. In addition, due to complicated acquisition procedures, the above technologies usually require operator attendance.

Fingerprint recognition is well-established and the most mature technology, however it has several drawbacks: the system cannot verify physical presence of the fingerprint owner and therefore is prone to deception, limiting its suitability for on-line applications; the optical sensor is a costly and fragile device, generally unsuitable for consumer markets; and it suffers from negative connotations related to criminology.

Retina scanning technologies are characterized by high performance. However, they require high-precision optical sensors, and are not user friendly as they require manipulation of head posture and operate on a very sensitive organ—the human eye. The optical sensor is costly and fragile.

Iris and face recognition systems are friendly technologies as they take an image from afar. However, they require digital photographic equipment and are sensitive to lighting conditions, as well as to pupil size variations and facial expressions, respectively. In addition, Iris recognition performance is degraded by dark glasses and contact lens usage, and face recognition may be deceived by impersonation.

Voice recognition is the most friendly technology, however it requires a low-noise setting and is highly sensitive to intrinsically variable speech parameters including intonation. Moreover, existing conventional recording technologies may be used to deceive speech based recognition systems.

Thus, a need exists for reliable and robust, hard to deceive (on-line and off-line), low cost, user friendly identity recognition technologies for stand alone applications as well as for integration with current security systems.

BRIEF SUMMARY OF THE INVENTION

According to the invention an individual is identified by:
producing and storing a first biometric signature that identifies a specific individual by forming the difference between a representation of the heartbeat pattern of the specific individual and a stored representation of common features of heartbeat patterns of a plurality of individuals;
after the producing step, obtaining a representation of the heartbeat pattern of a selected individual and producing a second biometric signature by forming the difference between the heartbeat pattern of the selected individual and the stored representation of the common features of the heartbeat patterns of the plurality of individuals; and
comparing the second biometric signature with the first biometric signature to determine whether the selected individual is the specific individual.

The stored representation of common features of heartbeat patterns of a plurality of individuals can be obtained by measuring and storing such representations and then averaging all of the stored representations, or employing techniques such as principal component analysis, wavelet decomposition, etc.

The individual can be a human or an animal.

Apparatus according to a preferred embodiment of the present invention performs automatic extraction of subject-specific bioelectric signals for the purpose of recognition of a person's identity. This apparatus can be incorporated into a wide range of devices and systems. A few non-limiting examples are: a smart card; a passport; a driver's license apparatus; a Bio-logon identification apparatus; a palm pilot; a cellular embedded identification apparatus; an anti-theft apparatus; an ECG monitoring apparatus, an e-banking apparatus, an e-transaction apparatus; a pet identification apparatus; a physical access apparatus; a logical access apparatus; and an apparatus combining ECG and Fingerprint monitoring. Other possibilities will be apparent to those skilled in the art.

Apparatus according to the invention can operate continuously or on demand. The apparatus can be constructed to obtain the representation of the heartbeat pattern of a selected individual by having electrodes that are contacted by either the hands or feet of the selected individual. When the apparatus of claim is provided in a smart card, the card can be enabled for a limited period of time after successful recognition and disabled thereafter until the next successful recognition is performed. The apparatus can be constructed to operate with encryption keys or digital signatures.

According to one embodiment of the invention, the apparatus can be incorporated into a watch worn on the wrist, where the signal is measured between the wrist on which the watch is worn and the other hand of the wearer. The back side of the watch may be made of a conductive medium (e.g. a metal plate) in contact with the back of the wrist, and the face of the watch can be provided with another metal contact that needs to be touched with a finger of the other hand. The watch may transmit a signal indicating confirmation of the identity of its wearer, and/or activating a physically or logically locked device such as a door, a computer, a safe, etc. Alternatively, the watch may transmit personal information about its wearer.

A method according to a preferred embodiment of the present invention is based on electro-cardiologic signal discrimination. Analysis is carried out synchronously with the heart beat, eliminating features common to the general population and thus enhancing subject-specific features that constitute an electro-biometric, or biometric, signature, normally undetectable in raw electro-cardiologic signals.

The method according to the invention is based on acquisition of bioelectric signals, which are transformed into unique electro-biometric signatures. The uniqueness of the electro-biometric signatures makes the system very difficult to deceive, and its inherent robustness makes it ideal for local as well as for remote and on-line applications. In addition, the system is characterized by high recognition performance, supporting both open and closed search modes. An open search is one in which many stored signatures are searched to identify one subject, a closed search is one in which one stored signature is examined to verify the identity of one subject. An important advantage of the electro-biometric system according to the invention is its simple and straight-forward acquisition technology, implying a low-cost, user friendly acquisition apparatus and eliminating the need for a skilled operator.

The invention is based on a novel electro-cardiologic signal acquisition, processing, and analysis. Generally, electrical signals generated by the heart can be picked up using conventional surface electrodes, usually mounted on the subject's chest. The signals are made up of several components representative of different functional stages during each heart beat, projected according to the electric orientation of the generating tissues. Even a slight change of electrode placement may cause drastic changes in the received signal morphology, to the extent of appearance or disappearance of distinct signal components.

The invention makes use of the fact that there exist electrode placement sites that produce subject-specific consistent signals, completely robust to changes of electrode placement within the sites. These sites are the arms and legs (including fingers and toes), which provide consistent, reproducible electro-cardiologic signals. The robustness to location variations in electrode placement within these sites stems from a constant electro-cardiologic signal projection which does not change as long as the electrodes remain close to a limb extremity.

Electro-cardiologic signals are affected by changes in pulse rate, which is a well-known electro-cardiologic modifier. Pulse rate changes may cause latency changes of the 'P' and 'T' components relative to the 'QRS' component of the electro-cardiologic signal (these components appear in FIG. 5). However, pulse rate changes may be automatically compensated for by retrospective, pulse rate driven adjustment of the signal complex. Moreover, an adaptive operation mode of the system can track and compensate for pulse rate induced changes. This can be done by compressing or expanding the time scale of one cycle of the heartbeat waveform. More sophisticated formulation describing the relations between waveform characteristics (e.g. S-T, P-Q segment durations) and pulse rate may be used.

Different persons present subject-specific detail in their electro-cardiologic signals due to normal variations in the heart tissue structure, heart orientation, and electrical tissue orientation, which reflect on the electro-cardiologic signals measured from the limbs. However, in an electro-cardiologic signal, the subject-specific detail is obscured by major electro-cardiologic features that are common to the general population. Elimination of these common features, according to the invention, reveals subject-specific detail and allows for high-performance recognition of a person, using an identification signature derived from an electro-cardiologic signal as a unique bioelectric signature.

BRIEF DESCRIPTION OF THE DRAWING

FIG. 1 is a simplified block diagram of a system according to the invention, composed of a signal acquisition module, a signal processing module, and an output module.

FIG. 2 is a block diagram of an embodiment of the signal acquisition module of the system of FIG. 1.

FIG. 3 is a block diagram of an embodiment of the signal processing module of the system of FIG. 1.

FIG. 4 is a diagram showing a grand-average electro-cardiologic signal waveform, which may serve as a template, calculated from a database of 20 subjects.

FIG. 5 shows a group of electro-cardiologic signal waveforms of ten of the subjects participating in the database and contributing to the average waveform of FIG. 4.

FIG. 6 shows a group of electro-biometric signature waveforms, or templates, derived from the signal waveforms of FIG. 5.

FIG. 7 shows a scatter plot and distribution histograms of the sign-maintained squared correlation values of the 20 subjects who contributed to the grand average waveform of FIG. 4.

DETAILED DESCRIPTION OF THE INVENTION

A preferred embodiment of a system according to the invention is designated an Electro-Biometric IDentification (E-BioID) system and is illustrated by way of example in FIG. 1. In this embodiment, the stored representation of the common features of the heartbeat patterns of the plurality of individuals is the average of the heartbeat patterns of the plurality of individuals. However, other embodiments can utilize stored representations of different types of common features, such as attainable with, for example, principal component analysis or wavelet decomposition In a preferred embodiment, the basic elements of the E-BioID system include a signal acquisition module 12, a signal processing module 14, and an output module 16, implemented in a single housing. In another preferred embodiment, remote analysis of locally acquired electro-biometric signals may be implemented by separating the functional elements for signal acquisition, processing, and output. Each of the components shown in FIG. 1 can be readily implemented by those skilled in the art, based on principles and techniques already well known in the art in combination with the present disclosure.

FIG. 2 shows a preferred form of construction of signal acquisition module 12 in an E-BioID system. The data acquisition module preferably includes a pair of sensors 22, pre-amplifiers 24; band-pass filters 26 and an analog-to-digital (A/D) converter 28. Each of these components can be readily implemented by those skilled in the art, based on principles and techniques already well known in the art in combination with the present disclosure.

Sensors 22 can be of any type capable of detecting the heartbeat pattern and can be, for example, metal plate sensors that can be connected as "add-on" onto a standard computer keyboard. The subject need only touch the sensors with two fingers.

FIG. 3 shows preferred elements of signal processing module 14 in the E-BioID system. The signal processing module preferably includes a Digital Signal Processor (DSP) 32, a Dual Port Ram (DPR) 34, an Electrically Erasable Programmable Read Only Memory ($E^2$PROM) 36 and an I/O port 38. Each of these components can be readily implemented by those skilled in the art, based on principles and techniques already well known in the art in combination with the present disclosure. Signal processing module 14 is connected to signal acquisition module 12 and output module 16 via port 38.

In an alternative embodiment, the signal processing module may be implemented, with suitable programming, on a personal computer, which is a flexible computation platform, allowing straight-forward integration of the system into existing computing facilities in a home, office, or institute/enterprise environments.

Output module 16 preferably consists of a dedicated display unit such as an LCD or CRT monitor, and may include a relay for activation of an external electrical apparatus such as a locking mechanism. Alternatively, the output module may include a communication line for relaying the recognition result to a remote site for further action.

Signal Acquisition, Processing and Analysis

Bioelectric signals, or heartbeat signals, are acquired in a simple manner, where the subject is instructed to touch two metal plates 22 for a few seconds. The metal plates conduct the bioelectric signals to the amplifiers 24, which amplify the bioelectric signals to the desired voltage range. In a preferred embodiment, the voltage range is zero to five volts.

The amplified signals pass through filters 26 to remove contributions outside a preferable frequency-range of 4 Hz–40 Hz. Alternatively, a wider range of 0.1 Hz–100 Hz may be used in conjunction with a notch filter to reject mains frequency interference (50/60 Hz). Digitization of the signal is preferably performed with a 12-bit A/D converter 28, at a sampling frequency of preferably about 250 Hz.

In module 14, the signals are normalized by the 'R' peak magnitude, to account for signal magnitude variations which mostly relate to exogenic electrical properties. The normalized data is transformed into an electro-biometric signature which is compared to pre-stored electro-biometric signature templates. The result of the comparison is quantified, optionally assigned a confidence value, and then transmitted to output module 16, which provides a recognition feedback to the user of the E-BioID system and may also activate external apparatuses such as a lock or siren, virtual apparatuses like network login confirmation, or a communication link.

In another embodiment, the E-BioID system is implemented as a fully integrated compact device, where many of the functional elements are implemented on an ASIC based system.

Principle of Operation

Biometric recognition requires comparing a newly acquired biometric signature against templates in a registered or enrolled biometric signature template database. This calls for two phases of operation of the system: Enrollment and Recognition.

Enrollment Phase

In a preferred embodiment, each new subject is instructed to touch two metal plates with two fingers, one of each hand. In alternative embodiments, the subject may touch the metal plates with other parts of the hands or legs. The system monitors the subject's pulse rate and initiates a recording, preferably lasting for at least 20 seconds. Shorter intervals may be used depending on the required level of accuracy. Once the recording is complete, the system performs a self-test to verify signature consistency by comparison of at least two biometric signatures, derived from two parts of the registered segment. The two parts may be two halves, or two larger, overlapping, segments. The two parts are used to derive two biometric signatures. If the self-test result is successful, enrollment of that subject is complete, and if unsuccessful the procedure is repeated. The successful recording is used for construction of an electro-cardiologic signal or a series of electro-cardiologic signals, which are added to an electro-cardiologic signal database.

The electro-cardiologic signals are transformed into a set of electro-biometric signature templates by eliminating features that are common to all of the subjects participating in the dataset, thereby enhancing subject-specific discriminating features.

In a preferred embodiment; the system creates a grand-average electro-cardiologic template, which is calculated by synchronous averaging of the normalized electro-cardiologic signals of the entire pool of subjects. The grand-average represents the above-mentioned common features, and thus subtraction of the grand-average from each one of the electro-cardiologic signals yields a set of distinct, subject-specific electro-biometric template signatures. In an alternative embodiment, other means for elimination of the common features may be used, such as a principal component analysis or wavelet decomposition.

In another preferred embodiment, the database is divided into several subsets, so as to maximize intra-subset similarity and inter-subset disparity, yielding several distinct grand-averages. The partition into subsets may be performed using standard pattern classification schemes such as linear classifiers, bayesian classifiers, fuzzy classifiers, or neural networks. The partition into subsets is useful in cases of large databases, to simplify and shorten the search process as well as to ensure the validity of the grand-average as an appropriate representative of similarity among the electro-cardiologic signals.

FIG. 4 shows an example of a grand-average, constructed from a pool of 20 subjects participating in the database.

FIG. 5 shows 10 examples of electro-cardiologic signals, and FIG. 6 shows the electro-biometric template signatures derived from the above electro-cardiologic signals, by elimination of features common to all the subjects included in the database. Specifically, each signature of FIG. 6 is obtained by subtracting the waveform of FIG. 4 from the corresponding signal of FIG. 5. It will be observed that while the original electro-cardiologic signals are highly similar, the derived electro-biometric signatures present markedly pronounced differences. These differences have been found to reflect inherently unique electro-cardiologic disparity which underlies the recognition capabilities of the E-BioID system.

Recognition Phase

In the recognition phase, the subject interacts with the system in a similar manner to that of the enrollment phase, however a shorter recording time in the order of a few seconds is sufficient.

In a preferred embodiment, the system executes a verification procedure (closed search): the system processes the acquired signals, forms an electro-biometric subject signature, adjusts the signature according to the pulse rate, and compares the adjusted electro-biometric signature with the subject's enrolled electro-biometric signature template.

In another preferred embodiment, the system executes an identification procedure (open search): the system repeats the comparison process for the entire or partitioned database, thereby providing identification of the matching identity.

The Comparison Process

In a preferred embodiment, the comparison is performed by calculation of a correlation coefficient, $\rho$, between an electro-biometric signature $\sigma_j$ and an electro-biometric signature template $\Phi_i$, as follows:

$$\rho = \frac{COV[\sigma_j, \Phi_i]}{\sqrt{VAR[\sigma_j] \cdot VAR[\Phi_i]}}.$$

The correlation coefficient is squared, maintaining its original sign: $\eta = \text{sign}(\rho) * |\rho|^2$. In an alternative embodiment, the comparison may be based on other similarity measures, such as RMS error between electro-biometric signatures.

The comparison may yield one or several correlation coefficients, depending on the mode of operation: closed search; or open search. In a closed search mode, the sign-maintained squared correlation coefficient ($\eta$) is used for making the recognition decision: a value greater than a preset threshold is regarded as a positive identification, or a match; borderline, near-threshold values may indicate a need for extended or repeated recording. In an open search mode, the largest sign-maintained squared correlation coefficient among all sign-maintained squared correlation coefficients yields the most likely subject identification, provided that the highest coefficient is above a selected threshold.

The preset threshold is derived from the required confidence level; higher desired confidence levels require higher thresholds. In one embodiment, sign-maintained squared correlation values larger than 0.8 are characteristic of a match and values lower than 0.7 are characteristic of a mismatch. Thus, sign-maintained squared correlation values higher than 0.8 may be considered as true matches and values lower than 0.7 as mismatches.

The upper diagram of FIG. 7 shows a scatter plot of sign-maintained squared correlation values, marking the 0.8 threshold with a dashed line. A clear separation between matches (circles) and mismatches (stars) is evident. The histograms in the other two diagrams provide a different view-of the powerful recognition capabilities of the E-BioID system, where it can be seen that the mismatches are concentrated around the zero value (no correlation) while matches are densely distributed near 1.0 (absolute correlation).

In alternative embodiments, more sophisticated decision schemes may be used such as multi-parameter schemes (e.g. fuzzy logic schemes), which use more than one distance measure; for example, multiple correlation values can be derived from segmented data analysis.

In a preferred embodiment, the system improves its performance with time by adding electro-cardiologic signals to the subject's database file when changes in the signals are encountered. In subsequent recognitions, the system processes the newly acquired signals, calculates the pulse rate, forms an electro-biometric subject signature, selects the enrolled electro-biometric signature template with the most similar pulse rate, and compares the new electro-biometric signature with the selected enrolled electro-biometric signature template.

In another preferred embodiment, the system uses signals acquired during long-term system operation to track possible variation in the enrolled subject electro-cardiologic signal, and if consistent changes occur the enrolled signal is automatically adjusted to reflect these changes. This tracking process compensates for gradual changes in the electro-cardiologic signal over long time periods, but does not compensate for fast, acute changes like those expected in connection with clinical heart conditions. In another embodiment, such acute changes may be reported to the subject indicating a need for medical consultation.

EXAMPLE

Enrollment Algorithm

The following is an example algorithm for the enrollment phase:

i. Let $x_i(n)$ represent a 20-second, 250 Hz digitized sample of the $i^{th}$ new subject, where n denotes discrete units of time.
ii. $x_i(n)$ is band-pass filtered in the range 4 Hz–40 Hz.
iii. The filtered signal is denoted $y_i(n)$.
iv. The filtered signal $y_i(n)$ is searched for QRS complexes, identifying the 'R' peaks as anchor points.
v. The filtered signal $y_i(n)$ is maintained or inverted to obtain positive 'R' peaks.
vi. The identified QRS complexes are counted to establish an average pulse rate reading $PR_i$.
vii. The filtered signal $y_i(n)$ is segmented around the anchor points, taking 50 samples before and 90 samples after each 'R' anchor point.
viii. Each data segment is normalized by the amplitude of the 'R' anchor point.
ix. The segments are aligned around the anchor points and averaged to produce the subject electro-cardiologic signal, denoted $s_i(n)$.
x. The subject electro-cardiologic signal $s_i(n)$ is adjusted according to the average pulse rate $PR_i$, by normalizing 'P' and 'T' latencies according to the pulse rate. The adjusted electro-cardiologic signal is denoted $v_i(n)$.
xi. The pulse rate adjusted subject's electro-cardiologic signal $v_i(n)$ is added to the database and is introduced into a grand-average $T(n)$.
xii. A set of electro-biometric signatures $\Phi_i$ is constructed by subtraction of the grand-average $T(n)$ from each of the pulse rate adjusted electro-cardiologic signals stored in the system database.

EXAMPLE

Recognition Algorithm

The following is an example an algorithm for the recognition phase:

i. Let $x_j(n)$ represent a 10-second, 250 Hz digitized sample of the tested subject.
ii. $x_j(n)$ is band-pass filtered in the range 4 Hz–40 Hz.
iii. The filtered signal is denoted $y_j(n)$.
iv. The filtered signal $y_j(n)$ is searched for the locations of QRS complexes, using the R peak as an anchor point.
v. The filtered signal $y_j(n)$ is maintained or inverted to obtain positive 'R' peaks.
vi. The identified QRS complexes are counted to establish an average pulse rate reading $PR_j$.

vii. The filtered signal $y_j(n)$ is segmented around the anchor points, taking 50 samples before and 90 samples after each anchor point.
viii. The segments are aligned around the anchor points and averaged to produce the subject electro-cardiologic signal, denoted $s_j(n)$.
ix. The subject electro-cardiologic signal $s_j(n)$ is normalized according to the average pulse rate $PR_j$. The pulse rate adjusted subject electro-cardiologic signal is denoted $v_j(n)$.
x. An electro-biometric signature $\sigma_j$ is constructed by subtraction of the grand-average $T(n)$ from the pulse rate adjusted electro-cardiologic signal $v_j(n)$.
xi. The correlation coefficients between the electro-biometric signature $\sigma_j$ and all the enrolled electro-biometric signatures $\Phi_i$ are calculated and squared, maintaining their original arithmetic sign.
xii. The largest sign-maintained squared correlation value is selected and compared to a preset threshold.
xiii. If the selected largest sign maintained squared correlation value is larger than the preset threshold then a positive match is indicated, and the subject is identified.

Thus, a method and apparatus of acquisition, processing, and analysis of electro-cardiologic signals for electro-biometric identity recognition may include any subset of the following enrollment and recognition steps:

Enrollment
  Acquisition, digitization, and storage of electro-cardiologic signals from subjects;
  a. Formation of an electro-cardiologic signal database;
  b. Partition of the template database into several subsets based on electro-cardiologic signal similarity;
  c. Construction of one or more grand averages;
  d. Derivation of subject-specific electro-biometric signatures.

Recognition
  Verification
  The newly captured electro-biometric signature is compared with the subject specific enrolled electro-biometric signature template;
  e. Correlation and confidence analysis of the newly captured subject electro-biometric signature with the relevant stored electro-biometric signature template;
  f. Display and registration of the recognition result and/or activation of a physical or virtual local/remote mechanism.
  Identification
  The newly captured electro-biometric signature is compared with all of the electro-biometric signature templates participating in the database;
  g. Correlation and confidence analysis of the newly captured subject electro-biometric signature with all stored electro-biometric signature templates;
  h. Display and registration of the recognition result and/or activation of a physical or virtual local/remote mechanism.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose-of description and not of limitation. The means, materials, and steps for carrying out various disclosed functions may take a variety of alternative forms without departing from the invention.

Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:
1. A method for identifying an individual, comprising:
  a preliminary step of obtaining representations of the heartbeat patterns of a plurality of individuals, and deriving and storing the representation of the common features of the heartbeat patterns of a plurality of individuals from at least a selected number of representations;
  producing and storing a first biometric signature that identifies a specific individual by forming the difference between a representation of the heartbeat pattern of the specific individual and the stored representation of common features of heartbeat patterns of a plurality of individuals;
  after said producing step, obtaining a representation of the heartbeat pattern of a selected individual and producing a second biometric signature by forming the difference between the heartbeat pattern of the selected individual and the stored representation of the common features of the heartbeat patterns of the plurality of individuals; and
  comparing said second biometric signature with the first biometric signature to determine whether the selected individual is the specific individual.

2. The method of claim 1 wherein:
  said step of producing and storing comprises producing and storing a plurality of first biometric signatures, each identifying a respective individual, by forming the difference between a representation of the heartbeat pattern of each respective individual and the stored representation of the common features of the heartbeat patterns; and
  said step of comparing is carried out with respect to each of said first biometric signatures.

3. The method of claim 2 wherein said step of comparing comprises correlating said second biometric signature with each of said first biometric signatures and identifying that one of said first biometric signatures that correlates most closely to said second biometric signature.

4. The method of claim 3, wherein said step of correlating comprises obtaining a correlation coefficient associated with each first biometric signature, and said step of comparing further comprises comparing the correlation coefficient associated with the identified first biometric signature with a correlation coefficient threshold.

5. The method of claim 1 wherein said step of deriving and storing the representation of the common features of the heartbeat patterns of a plurality of individuals comprises deriving and storing a plurality of representations of the common features of the heartbeat patterns each from a respectively different group of the plurality of individuals.

6. The method of claim 1, wherein said step of deriving and storing the representation of the common features of the heartbeat patterns of a plurality of individuals comprises producing an average of the heartbeat patterns of the plurality of individuals.

7. The method of claim 1, wherein said step of deriving and storing the representation of the common features of the heartbeat patterns of a plurality of individuals comprises performing one of principal component analysis or wavelet decomposition.

8. The method of claim 1 wherein said step of comparing comprises: correlating said second biometric signature with said first biometric signature to obtain a correlation coefficient; and comparing the correlation coefficient associated with the identified first biometric signature with a correlation coefficient threshold.

9. The method of claim 1 wherein said step producing and storing a first biometric signature comprises storing the signature in a local database.

10. The method of claim 1 wherein said step producing and storing a first biometric signature comprises storing the signature in a remote database.

11. The method of claim 1 wherein said step of obtaining a representation of the heartbeat pattern of a selected individual comprises compensating for deviations in the pulse rate of the selected individual from a selected pulse rate.

12. The method of claim 1 wherein said step of obtaining a representation of the heartbeat pattern of a selected individual comprises obtaining several representations of heartbeat patterns.

13. The method of claim 1 wherein said step of producing and storing a first biometric signature of a specific individual comprises obtaining a plurality of representations of the heartbeat pattern of the specific individual over a period of time and producing successive first biometric signatures each from a respective one of the plurality of representations of the heartbeat pattern of the specific individual.

14. Apparatus for identifying an individual, comprising:
means for producing and storing a first biometric signature that identifies a specific individual by forming the difference between a representation of the heartbeat pattern of the specific individual and a stored representation of common features of the heartbeat patterns of a plurality of individuals;
means for obtaining, after the first biometric signature has been produced and stored, a representation of the heartbeat pattern of a selected individual and producing a second biometric signature by forming the difference between the heartbeat pattern of the selected individual and the stored representation of the common features average of the heartbeat patterns of the plurality of individuals; and
means for comparing said second biometric signature with said first biometric signature to determine whether the selected individual is the specific individual.

15. The apparatus of claim 14 wherein:
said means for producing and storing comprises means for producing and storing a plurality of first biometric signatures, each identifying a respective individual, by forming the difference between a representation of the heartbeat pattern of each respective individual and the stored representation of the common features of the heartbeat patterns; and
said means for comparing is carried out with respect to each of said first biometric signatures.

16. The apparatus of claim 15 wherein said means for producing and storing comprises means for obtaining representations of the heartbeat patterns of a plurality of individuals, and means for deriving the stored representation of the common features from at least a selected-number of the representations.

17. The apparatus of claim 16 wherein said means for deriving comprises means for deriving a plurality of stored representations of the common features, each from a respectively different group.

18. The apparatus of claim 15 wherein said means for comparing comprises means for correlating said second biometric signature with each of said first biometric signatures and identifying that one of said first biometric signatures that correlates most closely to said second biometric signature.

19. The apparatus of claim 18, wherein said means for correlating comprises means for obtaining a correlation coefficient associated with each first biometric signature, and said means for comparing further comprises means for comparing the correlation coefficient associated with the identified first biometric signature with a correlation coefficient threshold.

20. The apparatus of claim 14 wherein said means for comparing comprises: means for correlating said second biometric signature with said first biometric signature to obtain a correlation coefficient; and means for comparing the correlation coefficient associated with the identified first biometric signature with a correlation coefficient threshold.

21. The apparatus of claim 14 wherein said apparatus is one of: a smart card; a passport; a driver's license apparatus; a Bio-logon identification apparatus; a palm pilot; a cellular embedded identification apparatus; an anti-theft apparatus; an ECG monitoring apparatus, an e-banking apparatus, an e-transaction apparatus; a pet identification apparatus; a physical access apparatus; a logical access apparatus; and an apparatus combining ECG and Fingerprint monitoring.

22. The apparatus of claim 14 wherein said apparatus is a Bio-logon identification apparatus for remote logon to secure resources.

23. The apparatus of claim 14 wherein said apparatus is continuously in operation.

24. The apparatus of claim 14 wherein said means for obtaining are constructed to be contacted by either the hands or feet of the selected individual.

25. The apparatus of claim 14 wherein said apparatus is provided in a smart card that is enabled for a limited period of time after successful recognition and disabled thereafter until the next successful recognition is performed.

26. The apparatus of claim 14 wherein said apparatus is constructed to operate with encryption keys or digital signatures.

27. The apparatus of claim 14 incorporated into a watch worn on the wrist, where the signal is measured between the wrist on which the watch is worn and the other hand of the wearer.

* * * * *